United States Patent [19]
Shaffner

[11] Patent Number: 4,566,208
[45] Date of Patent: Jan. 28, 1986

[54] TOE PROTECTOR

[76] Inventor: Richard L. Shaffner, 1640 Damon Ct., Atlanta, Ga. 30338

[21] Appl. No.: 613,273

[22] Filed: May 24, 1984

[51] Int. Cl.⁴ .............................................. A43B 7/00
[52] U.S. Cl. ...................................... 36/110; 36/112; 128/84 B; 128/581
[58] Field of Search ................. 36/110, 111, 112, 113, 36/109, 72 R, 132; 128/83.5, 82, 83, 581, 84 B, 84 C; 2/2.5, 81 R

[56] References Cited
U.S. PATENT DOCUMENTS

| | | | |
|---|---|---|---|
| 1,954,569 | 3/1934 | League | 36/72 R |
| 2,002,662 | 5/1935 | Hauer | 36/72 |
| 2,423,354 | 7/1947 | Van Hoesen | 128/83.5 |
| 2,973,590 | 3/1961 | Gaskill | 36/72 |
| 3,263,679 | 8/1966 | Hass | 128/83.5 |
| 3,583,397 | 6/1971 | Baddour | 128/84 C |
| 3,773,041 | 11/1973 | Bogar, Jr. et al. | 128/83.5 |
| 3,916,538 | 11/1975 | Loseff | 36/11.5 |
| 4,019,503 | 3/1977 | Smith | 128/83.5 |
| 4,061,138 | 12/1977 | Bernstein | 128/82 |
| 4,177,583 | 12/1979 | Chapman | 36/77 R |
| 4,271,605 | 6/1981 | Raczka | 128/581 |
| 4,454,872 | 6/1984 | Brouhard | 128/83.5 |

Primary Examiner—Henry S. Jaudon
Assistant Examiner—Mary A. Ellis
Attorney, Agent, or Firm—Thomas & Kennedy

[57] ABSTRACT

A toe protector has two guard rails (12) that are to be incorporated into opposite sides of a foot cast or mounted to the sides of an orthopedic shoe. The toe protector also has a pair of front rails (14) whose ends are configured to be releasably mounted by press fits to adjacent ends (21, 22) of the guard rails that jutt forward of the toes of a foot located within the cast or shoe.

11 Claims, 4 Drawing Figures

TOE PROTECTOR

TECHNICAL FIELD

This invention relates to toe protectors of the types adapted to be mounted to foot casts and to orthopedic shoes.

BACKGROUND OF THE INVENTION

Foot guards and toe protectors have been devised to provide foot protection for workers such as those who handle heavy articles or work with potentially dangerous equipment such as lawnmowers. Examples of foot protective devices are illustrated in U.S. Pat. Nos. 2,002,662 and 2,973,590. Other foot protective devices have been devised for use with foot casts and orthopedic shoes. For example, U.S. Pat. Nos. 3,263,679, 3,773,041 and 3,916,538 described toe protectors for use with walking heels that project downwardly from foot casts. These devices have ordinarily been of a cup-shaped form which are designed to be either releasably or permanently mounted to the cast heel.

More recently, an orthopedic shoe has been conceived that has a removable toe guard as described in U.S. Pat. No. 4,177,583. A toe protector has also been devised, as shown in U.S. Pat. No. 4,061,138, for use with an orthopedic cast which protector also has a removable toe guard. The provision of a removable section is advantageous for it enables a physician to gain temporary access to the exposed toes of a patient that project out of a foot cast or shoe for examination and treatment.

The last two mentioned types of devices have been designed for limited use with either a specially constructed orthopedic shoe or with an in situ formed cast. In general, toe protectors have been rather bulky and costly to manufacture. It therefore would be a distinct advance in the art were a toe protector to be devised that could be mounted to shoes of various constructions as well as to orthopedic foot casts while possessing the attributes of simplicity and economy. It is thus the provision of such a toe protector to which the present invention is primarily directed.

SUMMARY OF THE INVENTION

Briefly described, the present invention comprises a toe protector including two elongated side guard rails to be positioned adjacent opposite sides of a human foot and at least one elongated front guard rail to be positioned in front of the toes of the human foot. The toe protector also comprises means for releasibly coupling opposite ends of the front guard rail with end portions of the two side guard rails so as to form a generally U-shaped toe protector having side guard rails that are mounted to the sides of a foot cast or to a shoe, i.e. a foot covering and a front guard rail that is releasibly mounted to the two side guard rails while the side guard rails remain mounted to the foot cast or shoe.

The two side guard rails are adapted to be incorporated into a foot cast along opposite sides thereof or to be mounted to opposite sides of an orthopedic shoe with an end portion of each side guard rail jutting beyond the toes of a human foot located within the cast or within the shoe. The front guard rail is of a size to extend between the end portions of the side guard rails in front of the toes of the human foot.

The side guard rails each have parallel rails joined together with at least one post and with one end of each rail being inturned and formed in the shape of a cylindrical tip. The front guard rails comprise a pair of tubular railings whose ends are of a size and shape as to be press fitted over the inturned guard rail tips.

Therefore, it is an object of this invention to provide a protector for the toes of a human foot, with the protector having connector portions that are mounted to a cast or to a shoe and extend from the sides of the foot, out in front of the foot, and a portion extending about the toes which is releasably attached to the connector.

Another object of this invention is to provide a protector for the toes of a human foot which is inexpensive to construct and easy to mount to a cast or to an open toe orthopedic shoe, which has a removeable section extending about the toes of the foot and which does not hide the toes from visual examination.

Other objects, features and advantages will become apparent upon reading the following specification, when taken in conjunction with the accompanying drawings.

DETAILED DESCRIPTION

Figure 1:
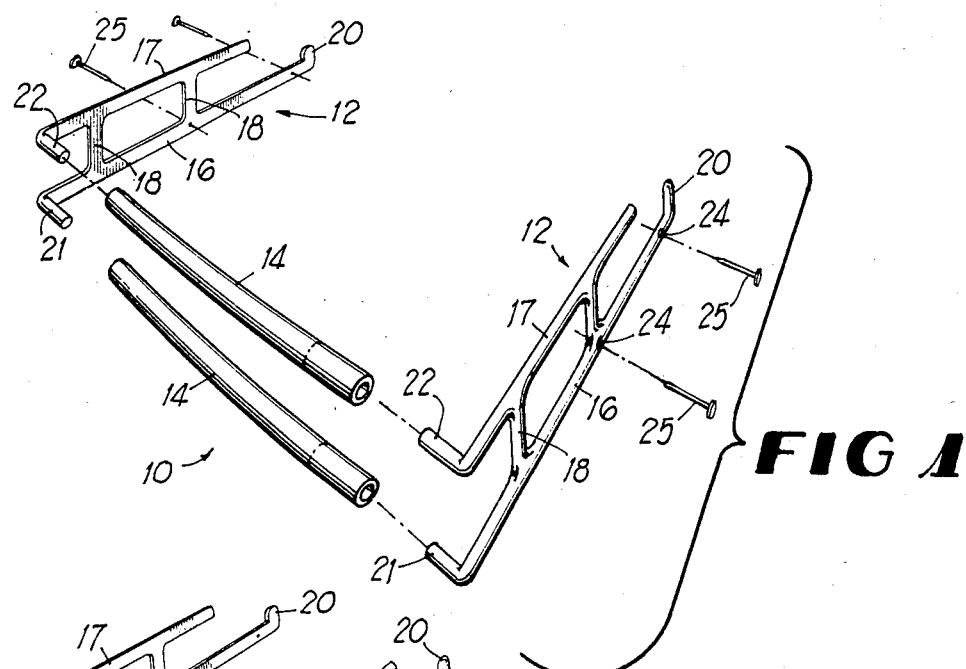
FIG. 1 is an exploded view, in perspective, of a toe protector embodying principles of the present invention in a preferred form.

Referring now in more detail to the drawings, in which like numerals indicate like parts throughout the several views, FIG. 1 illustrates the toe protector 10 which includes of two elongated side guard rails 12 two elongated front guard rails 14. Each of the two guard rails 12 is of unitary, plastic, slightly flexible construction so as to have a lower rail 16 and an upper rail 17 joined together by two upright posts 18. The inside faces of the guard rails that confront the wearer's foot, when assembled, are substantially flat whereas their outwardly facing surfaces are rounded. Each of the lower rails 16 has L-shaped end portions oriented at right angles with respect to one another, with a rear end portion formed with an upright anchor 20 and with a forward end portion formed with an inturned, cylindrical coupling tip 21. The forward end of each upper railing 17 adjacent a coupling tip 21 of the lower rail is also formed with an inturned, cylindrical coupling tip 22. Each of the lower rails 16 is formed with two small holes 24 through which tacks 25 are to be inserted. The front guard rails 14, which are of flexible, plastic construction have a uniformly tubular configuration whose end openings are of a size to receive snugly, in a press fitting manner, the coupling tips 21/22 of the side guard rails 12. Preferably, each of the railings 14 is formed with a slight outward bow. When the side guard rails 12 are mounted to the foot, they usually diverge from each other at the front of the foot, and when the front guard rails 14 are mounted at their ends to side guard rails 12, the front guard rails tend to bow slightly.

Figure 2:
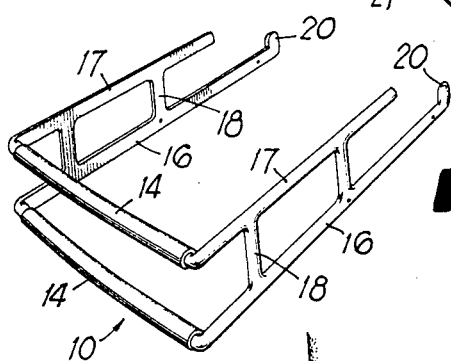
FIG. 2 is a perspective view of the toe protector illustrated in FIG. 1 shown in an assembled configuration.

So constructed, the two guard rails, the two railings, and a supply of tacks are packaged for sale of the toe protector in a disassembled configuration. Later, as hereinafter described, these components are readily assembled to form a toe protector of a generally U-shaped configuration as shown in FIG. 2 by telescopically press fitting the ends of the railings over the coupling tips of the guard rails.

Figure 3:
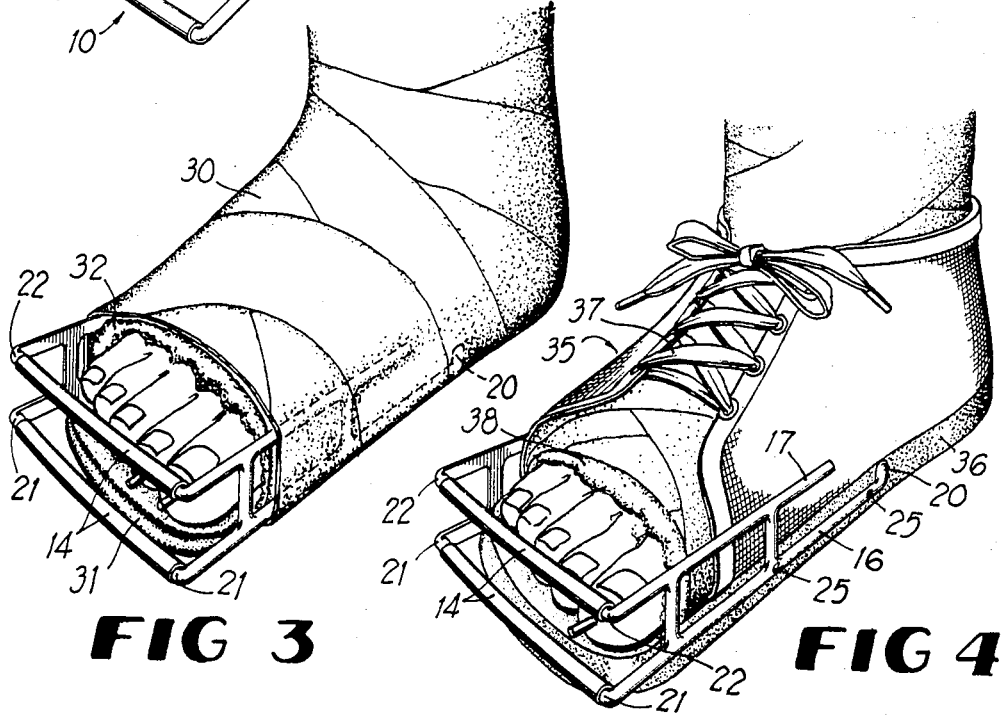
FIG. 3 is a perspective view of the toe protector illustrated in FIGS. 1 and 2 shown assembled and incorporated into a foot cast.

For use, the toe protector 10 is readily mounted either to a foot cast or to a shoe of most any conventional shape. For example, as shown in FIG. 3, the toe protector is incorporated into a foot cast 30. This is done by first wrapping conventional orthopedic casting material about a human foot covered with padding 32 and about a foot pad 31 upon which the foot is placed while ordinarily leaving at least the tops and sides of the toes exposed. The two side guard rails 12 are then placed against opposite sides of the partially formed cast with the coupling tips 21 and 22 jutting beyond the area of the toes and being mutually aligned. Additional casting material is then wrapped about the foot and foot pad over the previously wrapped material and over a portion of the two side guard rails. The casting material is then allowed to coalesce with each side rail firmly and securely incorporated into the cast. A portion of a lower and an upper rail 16 and 17, a post 18 and an L-shaped anchor 20 of each side guard rail is incorporated into the cast inhibits any movement of a guard rail with respect to the cast after the cast has been set. The two tubular front guard rails 14 are press fitted onto the coupling tips 21 and 22 by spreading the flexible side guard rails and placing the tubular front rails in position, whereupon the assembly of foot, cast and toe protector appears as shown in FIG. 3.

Figure 4:
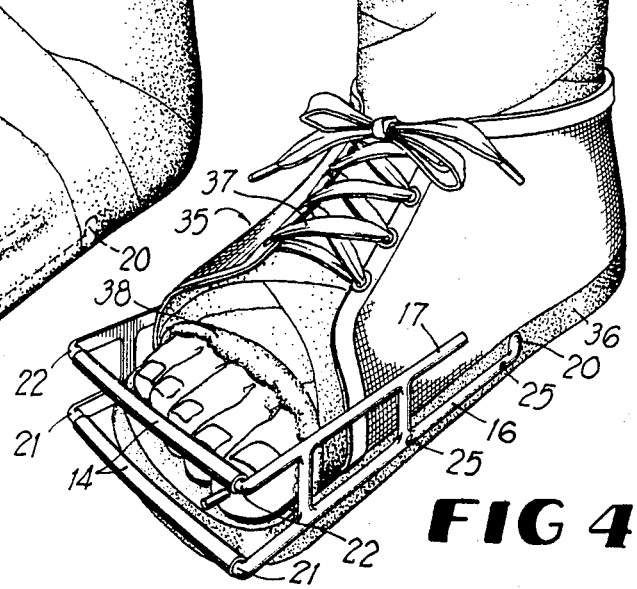
FIG. 4 is a perspective view of the toe protector illustrated in FIGS. 1 and 2 shown assembled and mounted to a shoe.

Alternatively, the toe protector can be readily mounted to an orthopedic shoe such as that shown in FIG. 4 having an open toe area. This is done by positioning each of the side guard rails against a side of the shoe as illustrated in FIG. 4 with the coupling tips 21 and 22 of each rail jutting beyond the front of the shoe. The side guard rails are then mounted securely to the shoe by passing tacks 25 through rail holes 24 and nailing them into the sole 36 of the shoe. The tubular front railings 14 are then mounted to the coupling tips 21 and 22 of the side guard rails by spreading the flexible front portions of the side guard rails and inserting the front rails between them and then pressing the side guard rails back to their normal positions. Once a foot is inserted into the shoe 35 atop sole 36 in intimate contact with the padding or lining material 38 and laces 37 tied, the overall assembly assumes the posture illustrated in FIG. 4.

The front guard rails 14 can be shortened by cutting off some of one end portion. This permits the toe protector to be adjusted to fit narrow feet. When the toe protector has been applied to a foot as illustrated in FIGS. 3 and 4, the toes are readily visible by the patient and the physician without requiring removal of the front guard rails. Moreover, the front guard rails are removeable by simply spreading the front portions of the side guard rails.

Thus a toe protector is provided of a novel configuration that comprises relatively simple and inexpensive components which may be used equally well with foot casts and with orthopedic or even street shoes. Once mounted to a cast or to a shoe the front guard rails can be readily dismounted to provide access to the protected toes as for medical examination and treatment. Later, the railings may then be replaced to provide continued toe protection.

It should, of course, be understood that the just described embodiment merely illustrates principles of the invention in a preferred form. Many modifications, additions and deletions may be made thereto without departure from the scope of the invention as set forth in the following claims.

I claim:

1. A toe protector comprising, in combination, two elongated guard rails adapted for positioning adjacent opposite sides of a human foot, at least one elongated front rail adapted for positioning in front of the toes of the human foot, and means for releasibly coupling opposite ends of said front rail with end portions of said two guard rails so as to form a generally U-shaped toe protector having guard rails that are mountable to the sides of a foot covering and a front rail that is releasibly mountable to the two guard rails while the guard rails remain mounted to the foot covering.

2. The toe protector of claim 1 wherein each of said guard rails comprises two rails unitarily joined together by at least one post.

3. The toe protector of claim 2 wherein an end portion of each of said guard rail rails is generally L-shaped and formed with a cylindrical tip, and wherein said front rail has hollow cylindrical ends sized to be press fitted about said guard rail cylindrical tips.

4. The toe protector of claim 3 wherein another end portion of one of said guard rail rails opposite said first end portions is formed with an L-shaped anchor oriented substantially at a right angle with respect to said one L-shaped end portion.

5. The toe protector of claim 1 wherein each of said guard rails and said front rail consists essentially of plastic.

6. The toe protector of claim 1 wherein each of said guard rails is formed with at least one hole through which a tack is to be inserted to secure the guard rails to a shoe.

7. A toe protector comprising, in combination, two guard rails adapted to be incorporated into a foot covering along opposite sides thereof with an end portion of each guard rail jutting beyond the toes of a human foot located within the foot covering and at least one front rail of a size to extend between said two guard rail end portions in front of the toes of the human foot, and wherein said two guard rail end portions and the ends of said rail are formed with means for releasibly coupling together said guard rails and rail and wherein said front rail consists essentially of a plastic tube.

8. A toe protector comprising a pair of guard rails with each guard rail having two parallel rails joined together by at least one post and with one end of each rail being inturned and having a cylindrical tip, and a pair of tubular rail whose ends are of a size and shape as to be press fitted over said inturned rail ends of said guard rails.

9. The toe protector of claim 8 wherein each of said guard rails and each of said rails is of unitary, plastic construction.

10. A toe protector for mounting about the toes of a human foot comprising a pair of side support members for connection to the opposite sides of a foot covering, said side support members each including front portions for protruding on opposite sides of the foot beyond the toes of the foot, and a toe guard for positioning in front of the toes, said toe guard including means for removably mounting said toe guard to the protruding ends of said side support members, whereby the side support members are permanently mounted at the sides of the foot and the toe guard is removably mounted at the front of the foot.

11. The toe protector of claim 10 and wherein said side support members are flexible, and said means for removeably mounting said toe guard to the protruding ends of said side support members comprises means for removing said toe guard from said side support members upon spreading said side support members.

* * * * *